(12) United States Patent
Oonuki et al.

(10) Patent No.: US 7,728,158 B2
(45) Date of Patent: Jun. 1, 2010

(54) PPAR ACTIVITY REGULATORS

(75) Inventors: Akiko Oonuki, Kawasaki (JP);
Toshihiko Yoshimura, Kawasaki (JP);
Katsumi Maezono, Kawasaki (JP);
Yayoi Kawato, Kawasaki (JP);
Hideyuki Tanaka, Kawasaki (JP);
Naoyuki Fukuchi, Kawasaki (JP);
Nozomu Ishida, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/753,967

(22) Filed: May 25, 2007

(65) Prior Publication Data

US 2007/0276041 A1 Nov. 29, 2007

(30) Foreign Application Priority Data

May 25, 2006 (JP) ............................. 2006-145621

(51) Int. Cl.
*C07C 233/00* (2006.01)
*A61K 31/195* (2006.01)

(52) U.S. Cl. ........................... 554/36; 554/35; 514/563

(58) Field of Classification Search ................ 564/35, 564/36, 45, 204; 514/558, 563; 554/36, 554/35

See application file for complete search history.

(56) References Cited

U.S. PATENT DOCUMENTS 6,090,250 A * 7/2000 Mazzeo et al. .............. 204/451

OTHER PUBLICATIONS http://en.wikipedia.org/wiki/Prodrug (2 pages).*
Han et al. et al., Targeted Prodrug Design to Optimize Druge Delivery, 2000, AAPS pharmsci, vol. 2, (1), article 6, pp. 1-11.*
http://en/ikipedia.org/siki/Levopoda(5 pages).*
Delerive et al., Peroxisome proliferator-activated receptors in inflammation control, 2001, (Journal of Endocrinology, vol. 169, pp. 453-459).*
Grunell et al., The Metabolic Syndrome: Peroxisome Proliferator-activated Receptor gamma and its Therapeutic Modulation, 2003, Journal of Clinical Endocrinology & Metabolism, 88(6), pp. 2412-2421.*
Jiang et al., Lingands of Peroxisome Proliferator-activated Receptro Inhibit Homocysteine-induced DNA Methylation of Inducible Nitric Oxide Synthase Gene, 2007, Acta Biochemica et Biophysica Sinica, 39(5), pp. 366-376.*
Rakic et al., Peroxisome Proliferator-Activated Receptro alpha Antagonism Inhibits Hepatitis C Virus Replication, 2006, Chemistry & Biology, 13, pp. 23-30).*
Williams et al., Peroxisome proliferator-Activated Receptro-alpha, Activation Reduces Salt-Dependent Hypertension dur9ign Chronic Endothelin B Receptor Blockade, Aug. 2005 Hypertension, pp. 366-371.*
Zhao et al., Peroxisome proliferator activated receptro-gama in pathogenesis of experimental fatty liver disease, 2004, World Journal of Gastroenterology, 10(9), pp. 1329-1332.*
Evan, R. M., et al., "PPARs and the Complex Journey to Obesity," Nature Medicine, vol. 10, No. 4, Apr. 2004, pp. 1-7.
Henke, B. R., "Peroxisome Proliferator-Activated Receptor α/γ Dual Agonists for the Treatment of Type 2 Diabetes," J. Med. Chem., 47, 2004, pp. 4118-4127.
Skrumsager, B. K., et al., "Ragaglitazar: The Pharmacokinetics, Pharmacodynamics, and Tolerability of a Novel Dual PPAR α and γ Agonist in Healthy Subjects and Patients with Type 2 Diabetes," J. Clin. Pharmacol., 43, 2003, pp. 1244-1256.

* cited by examiner

*Primary Examiner*—Shailendra Kumar
*Assistant Examiner*—Yate' K Cutliff
(74) *Attorney, Agent, or Firm*—Oblon, Spivak, McClelland, Maier & Neustadt, L.L.P.

(57) ABSTRACT

The object of the present invention is to provide PPAR (peroxisome proliferator-activated receptor) activity regulators, which can be widely used for improving insulin resistance and preventing/treating various diseases such as diabetes, metabolic syndromes, hyperlipemia, high-blood pressure, vascular disorders, inflammation, hepatitis, fatty liver, liver fibrosis, NASH (non-alcoholic steatohepatitis) and obesity.

The present invention provides PPAR activity regulators which comprise an acylamide compound having the specific structure, prodrugs thereof, or pharmaceutically acceptable salts thereof.

26 Claims, No Drawings

PPAR ACTIVITY REGULATORS

CROSS REFERENCES TO RELATED APPLICATIONS

This application claims priority to Japanese Patent Application 2006-145621, filed on May 25, 2006.

TECHNICAL FIELD OF THE INVENTION

The present invention relates to PPAR (peroxisome proliferator-activated receptor) activity regulators and PPAR activators, which can be widely used for improving insulin resistance and preventing/treating various diseases such as diabetes, metabolic syndromes, hyperlipemia, high-blood pressure, vascular disorders, inflammation, hepatitis, fatty liver, liver fibrosis, NASH (non-alcoholic steatohepatitis) and obesity. In addition, it also relates to dual activators of PPAR-α and PPAR-γ.

BACKGROUND OF THE INVENTION

Among the diseases widely called as adult diseases or life-style related diseases, those such as abnormal carbohydrate/lipid metabolisms, impaired glucose tolerance/diabetes/hyperlipemia/high-blood pressure related thereto, and abdominal obesity form clusters of the diseases, and are recognized as syndromes such as metabolic syndromes and insulin resistance syndromes, or visceral steatosis, syndrome X and the like. Patients with these syndromes not only have a low quality of life but also have higher lethal risk or a risk of developing fatal vascular disorders such as arterial sclerosis as compared with healthy people. Compounds having a thiazolidine structure such as rosiglitazone and pioglitazone, which have been recently found as antidiabetic agents, have a strong effect of improving insulin resistance and are expected to be applied to the treatment of the above syndromes in addition to diabetes (Non-patent Literature 1). The mechanism of these compounds having a thiazolidine structure is the agonist activity to PPAR-γ that is a transcription factor, and other compounds without a thiazolidine structure are also found as PPAR-γ agonists. PPAR-γ agonists or antagonists are expected to be applied to the diseases relating to insulin resistance or metabolic syndromes, for example, prevention/treatment of metabolic diseases, e.g. diabetes, gestational diabetes mellitus and polycystic ovary syndrome; prevention/treatment of cardiovascular diseases, e.g. ischemic heart disease, myocardial infarction, angina pectoris, and coronary artery cardiovascular disease; prevention/treatment of liver diseases, e.g. non-alcoholic/nonviral steatohepatitis and fatty liver disease (NASH and NAFLD); and prevention/treatment of malignant neoplasm and cancers such as large bowel cancer. Further, it has been reported that PPAR-γ agonists have a direct anti-atherogenic action and an immunoregulatory activity via immunocompetent cells such as monocytes.

On the other hand, since PPAR-γ agonists have unfavorable side-effects such as edema and weight gain, it is desired to develop PPAR-γ agonists without such side-effects. Meanwhile, fibrate agents such as clofibrate, fenofibrate and bezafibrate are antihyperlipemic agents and have the agonistic action to PPAR-α that is a transcription factor. Though it is known that PPAR-α agonists other than fibrate agents also have the antihyperlipemic action, they hardly have the antihyperglycemic action. Thus, PPAR-α agonists having a strong antihyperglycemic action are desired as therapeutic agents of a wide range of metabolic diseases such as metabolic syndromes. As mentioned above, it is obvious that the compounds that have the interaction with PPAR-α or PPAR-γ are useful. In addition to it, the agents that have the interactions with both PPAR-α and PPAR-γ can be expected to be useful for the wider range of patients since such agents have both the antihyperlipemic action due to their action to PPAR-α and the antidiabetic action due to their action to PPAR-γ (Non-patent Literature 2). Further, it is thinkable that the weight gain due to the PPAR-γ action is diminished by the effect of promoting the use of in vivo lipids due to the PPAR-α action. Dual agonists of PPAR-α and PPAR-γ have not been placed on the market in Japan. In other countries, low molecular compounds reported as having the dual agonistic action, such as muraglitazar, tesaglitazar, ragaglitazar, TAK-559 and GW-1536, have been clinically examined. However, the development of ragaglitazar, TAK-559 and GW-1536 was suspended because of the problems in the safety tests on animals. Though the effect of the dual agonists has been clinically examined, all of the problems seen in PPAR-γ agonists such as edema and weight gain have not been improved (Non-patent Literature 3). Thus, it is thought that the dual agonists still have the problems to be improved on safety thereof. Therefore, at present, it is desired to develop PPAR activity regulators such as PPAR-α agonists, PPAR-γ agonists and PPAR-α, γ dual agonists, which have good medicinal effects and high safety.

[Non-patent Literature 1] Evans R. M. et al.: PPARs and the complex journey to obesity. Nature Medicine 10 p 1-7, 2004.

[Non-patent Literature 2]1 Henke B. R.: Peroxisome proliferator-activated receptor α/γ dual agonists for the treatment of type 2 diabetes. J Med Chem 47 p 4118-4127, 2004.

[Non-patent Literature 3] Skrumsager B. K. et al.: Ragaglitazar: the pharmacokinetics, pharmacodynamics, and tolerability of a novel dual PPAR alpha and gamma agonist in healthy subjects and patients with type 2 diabetes.: J Clin Pharmacol 43 p 1244-56, 2003.

DISCLOSURE OF THE INVENTION

The object of the present invention is to provide PPAR activity regulators.

The further object of the present invention is to provide PPAR activators.

The additional object of the present invention is to provide PPAR-α, γ dual activators.

The inventors searched substances having PPAR-α or PPAR-γ agonist activity with the reporter assay using cultured cells, and found that specific acylamide compounds have PPAR-α or PPAR-γ agonist activity and some of them are dual agonists having both activities. The present invention has been completed based on this finding.

Namely, the present invention provides a PPAR activity regulator which comprises an acylamide compound of the formula (1), prodrugs thereof, or pharmaceutically acceptable salts thereof:

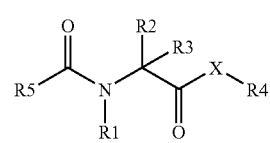

Formula (1)

wherein R1 is a hydrogen atom or an alkyl group having 1 to 6 carbon atoms; R2 is an alkyl group having 1 to 10 carbon atoms, aryl group having 6 to 10 carbon atoms, heteroaryl group having 1 to 10 carbon atoms, arylalkyl group having 7 to 20 carbon atoms, heteroarylalkyl group having 2 to 11 carbon atoms or alkylthioalkyl group having 2 to 6 carbon atoms;

R3 is a hydrogen atom or an alkyl group having 1 to 6 carbon atoms, and R2 and R3 may bond each other to form a ring;

R4 is a hydrogen atom or an alkyl group having 1 to 16 carbon atoms;

R5 is a straight-chain hydrocarbon group having 5 to 21 carbon atoms which may include 1 to 3 double bond(s); and X is an oxygen atom or NH.

The present invention also provides a PPAR-α agonist, PPAR-γ agonist, dual agonist of PPAR-α and PPAR-γ, or PPAR activator, which comprises the above acylamide compound, prodrugs thereof, or pharmaceutically acceptable salts thereof.

The present invention can control or activate activities of peroxisome proliferator-activated receptor (PPAR) that relate to insulin resistance or various diseases such as diabetes, metabolic syndromes, hyperlipemia, high-blood pressure, vascular disorders, inflammation, hepatitis, fatty liver, liver fibrosis, NASH (non-alcoholic steatohepatitis) and obesity by using a PPAR activity regulating or activating effect that the acylamide compound of the formula (1), prodrugs thereof, or pharmaceutically acceptable salts thereof have. Therefore, the effects of the present invention on the above diseases are expected beyond those of the existing therapeutic agents.

BEST MODE FOR CARRYING OUT THE INVENTION

Regarding the acylamide compounds of the formula (1), in the formula (1), an alkyl group includes a straight-chain, branched-chain or cyclic alkyl group. It may have a substitutent(s) such as a halogen atom and a hydroxyl group, but an alkyl group without these substitutents is preferable.

An aryl group represents a mono-, bi- or tri-cyclic aromatic substitutent composed of carbon atoms and preferably a mono or bi-cyclic aromatic substitutent. Its examples include a phenyl group, indenyl group, naphthyl group and fluorenyl group, and a phenyl group is preferable. An aryl group may have a substitutent(s) such as a lower alkyl group, lower alkoxy group, a halogen atom and hydroxyl group.

A heteroaryl group represents an aromatic heterocyclic substitutent consisting of 1 to 3 ring(s) each comprising 5 to 7 members of carbon and nitrogen, oxygen, sulfur or the like. For example, it includes a pyridyl group, pyridazinyl group, pyrimidinyl group, pyrazinyl group, pyrrolyl group, furanyl group, thienyl group, oxazolyl group, isoxazolyl group, pyrazolyl group, imidazolyl group, thiazolyl group, isothiazolyl group, thiadiazolyl group, indolyl group, isoindolyl group, benzofuryl group, isobenzofuryl group, benzothienyl group, benzopyrazolyl group, benzoimidazolyl group, benzoxazolyl group, benzothiazolyl group, quinolyl group, isoquinolyl group, naphthyridinyl group and quinazolyl group.

An arylalkyl group indicates an alkyl group substituted with one or more aryl group(s), and the substitution position thereof is not particularly limited.

An alkyl group in an arylalkyl group, heteroarylalkyl group and alkylthioalkyl group is preferably a straight- or branched-chain alkyl group. Examples of an aryl group in the arylalkyl group are those mentioned in the above "aryl group", and specifically a phenyl group. Examples of a heteroaryl group in the heteroarylalkyl group are those mentioned in the above "heteroaryl group."

Examples of a straight-chain hydrocarbon group include a straight-chain alkyl group, straight-chain alkenyl group and straight-chain alkynyl group. A straight-chain alkenyl group preferably has one or two unsaturated bond(s) in the molecule. These straight-chain hydrocarbon groups may have a substitutent(s) such as a halogen atom and a hydroxyl group, but those without these substitutents are preferable.

In the formula (1), R1 is preferably a hydrogen atom or an alkyl group having 1 to 4 carbon atoms; said alkyl group is preferably a straight or branched chain; and particularly preferably a straight-chain alkyl group.

R2 is preferably an alkyl group having 1 to 4 carbon atoms, phenylalkyl group having 7 to 8 carbon atoms or alkylthioalkyl group having 2 to 4 carbon atoms. Here, the alkyl group is preferably a straight or branched chain.

R3 is preferably a hydrogen atom or an alkyl group having 1 to 4 carbon atoms. Here, the alkyl group is preferably a straight or branched chain.

Here, in the formula (1), it is preferable that a structural part wherein R1 to R3 bond is derived from an amino acid selected from the group consisting of Ile, Leu, Val, Phe, Ala and Met. It is further preferable that it is derived from a DL- or L-amino acid. Among them, it is particularly preferable that it is derived from an L-amino acid.

R4 is preferably a hydrogen atom, a straight- or branched-chain alkyl group having 1 to 4 carbon atoms, cyclic alkyl group having 3 to 8 carbon atoms, or straight- or branched-chain alkyl group having 10 to 16 carbon atoms.

R5 is preferably a straight-chain alkyl group having 5 to 21 carbon atoms or alkenyl group which includes one or two double bond(s).

Further, in the present invention,

[2] it is preferable in the formula (1) that R1 is a hydrogen atom or an alkyl group having 1 to 4 carbon atoms; R2 is a straight- or branched-chain alkyl group having 1 to 4 carbon atoms, phenylalkyl group having 7 to 8 carbon atoms or alkylthioalkyl group having 2 to 4 carbon atoms; R3 is a hydrogen atom or an alkyl group having 1 to 4 carbon atoms; R4 is a hydrogen atom or an alkyl group having 1 to 4 carbon atoms; R5 is a straight-chain alkyl group having 5 to 21 carbon atoms which may include one double bond; and X is an oxygen atom.

[3] In above [2], it is preferable that R1 is a hydrogen atom or an alkyl group having 1 to 4 carbon atoms; R2 is a straight- or branched-chain alkyl group having 1 to 4 carbon atoms, phenylalkyl group having 7 to 8 carbon atoms or alkylthioalkyl group having 2 to 4 carbon atoms; R3 is a hydrogen atom; R4 is a hydrogen atom; and R5 is a straight-chain alkyl group having 5 to 21 carbon atoms which may include one double bond.

[4] In above [2], it is preferable that R1 is a hydrogen atom or an alkyl group having 1 to 4 carbon atoms; R2 is a straight- or branched-chain alkyl group having 1 to 4 carbon atoms, phenylalkyl group having 7 to 8 carbon atoms or alkylthioalkyl group having 2 to 4 carbon atoms; R3 is an alkyl group having 1 to 4 carbon atoms; R4 is a hydrogen atom; and R5 is a straight-chain alkyl group having 5 to 21 carbon atoms which may include one double bond.

[5] It is preferable in the formula (1) that R1 is a hydrogen atom or an alkyl group having 1 to 4 carbon atoms; R2 is a straight- or branched-chain alkyl group having 1 to 4 carbon atoms; R3 is a hydrogen atom; R4 is a hydrogen atom or a straight-chain, branched-chain or cyclic alkyl group having 1 to 16 carbon atoms; R5 is a straight-chain alkyl group having 5 to 21 carbon atoms which may include one double bond; and X is NH.

The present invention preferably comprises acylamide compounds of the following structural formulae, prodrugs thereof, or pharmaceutically acceptable salts thereof:

Formula (2)
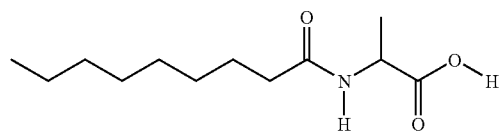

Formula (3)
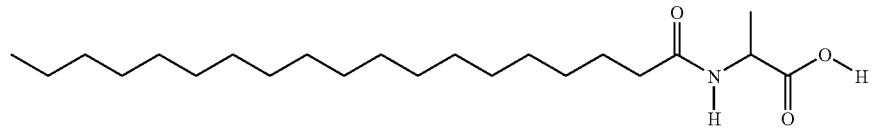

Formula 4)
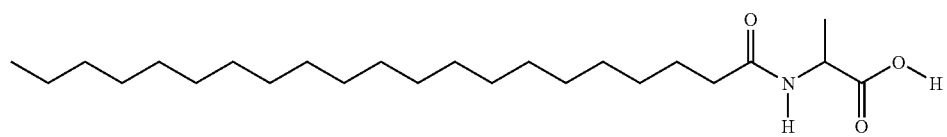

Formula (5)
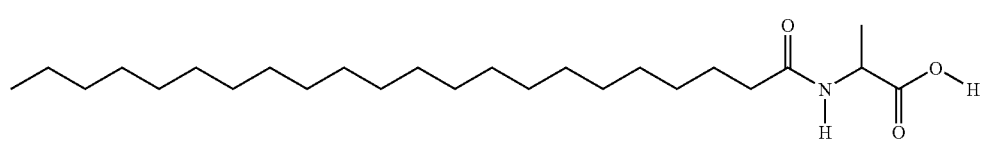

Formula (6)
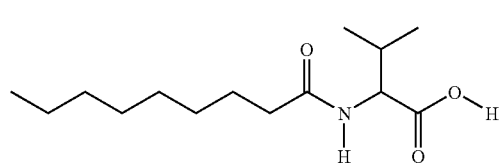

Formula (7)
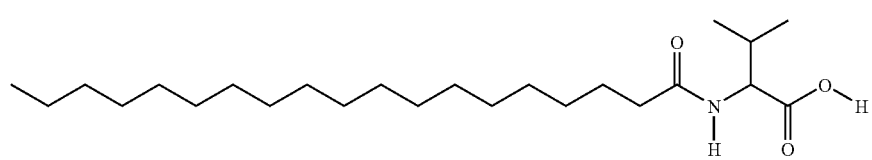

Formula (8)
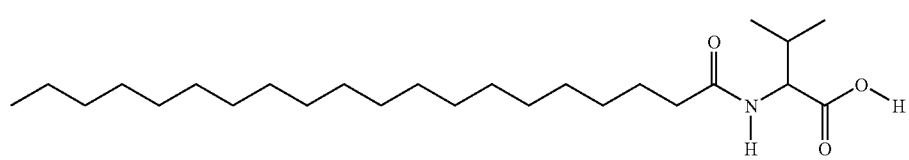

Formula (9)
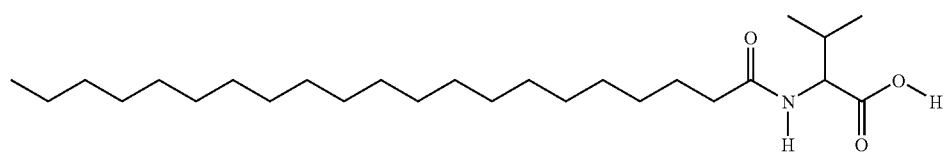

Formula (10)
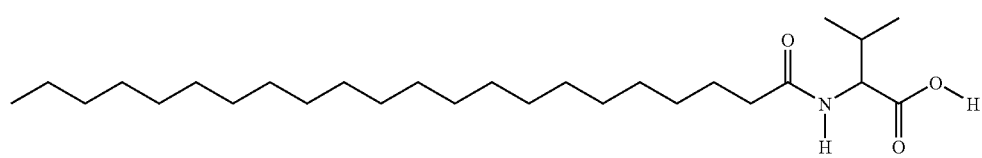

Formula (11)
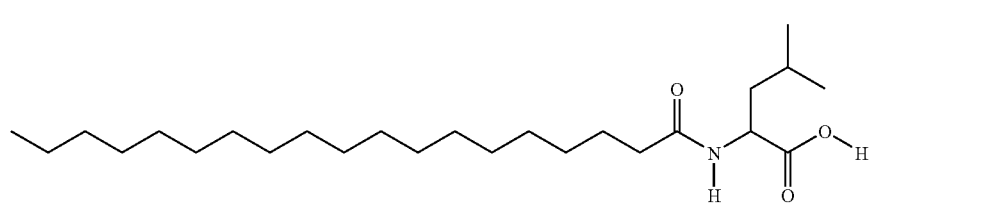

-continued

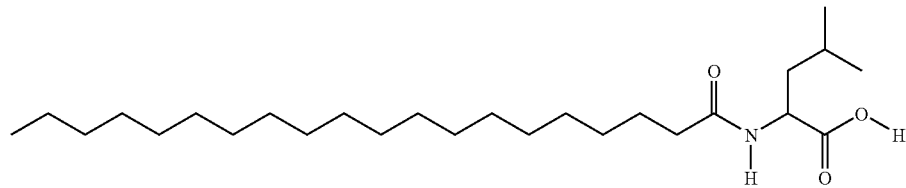

Formula (12)

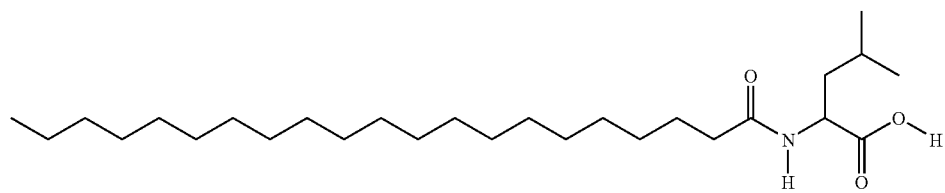

Formula (13)

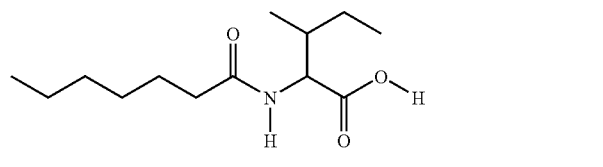

Formula (14)

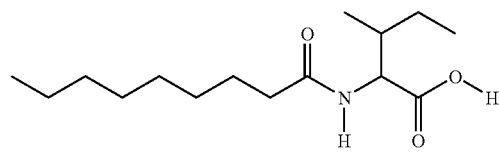

Formula (15)

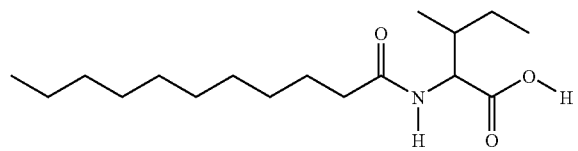

Formula (16)

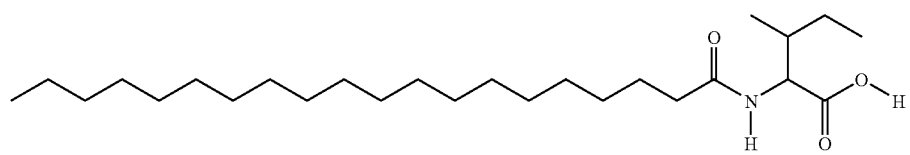

Formula (17)

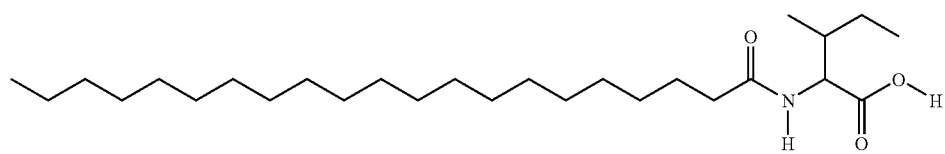

Formula (18)

When the acylamide compounds of the present invention can form salts thereof, it is sufficient for the salts to be pharmaceutically accepted ones and preferably medicinally acceptable ones. For example, to an acidic group(s) in case that the acidic group(s) exists in the acylamide compound, the examples include ammonium salts, and salts with alkali metals, e.g. sodium and potassium, salts with alkaline earth metals, e.g. calcium and magnesium, salts with aluminum and zinc, salts with organic amines, e.g. triethylamine, ethanolamine, morpholine, piperidine and dicyclohexylamine, and salts with basic amino acids, e.g. arginine and lysine. To a basic group(s) in case that the basic group(s) exists in the acylamide compound, the examples include salts with inorganic acids, e.g. a hydrochloric acid, sulfuric acid and phosphoric acid, salts with organic carboxylic acids, e.g. an oxalic acid, acetic acid, citric acid, malic acid, benzoic acid, maleic acid, fumaric acid, tartaric acid, succinic acid and glutamic acid, and salts with organosulfonic acids, e.g. methanesulfonic acid and p-toluenesulfonic acid. The salts can be formed by mixing the compound with a necessitated acid or base in a proper ratio in a solvent or dispersant, or by the cation exchange or anion exchange with another salt.

The compounds of the present invention include solvates thereof such as hydrates and alcohol adducts thereof. In addition, the compounds of the present invention also include prodrugs thereof.

Among the compounds of the formula (1), an N-acylamino acid wherein X=0 can be produced, for example, by reacting a corresponding amino acid with an acid chloride(s) as mentioned in Japanese Patent Unexamined Publication No. Sho 29-006713 or J. Am. Chem. Soc., vol. 78, p. 172 (1956).

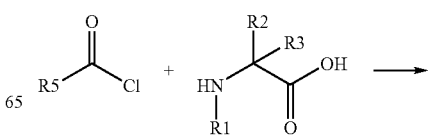

-continued

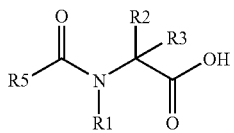

Further, among the compounds of the formula (1), N-acylamino-acid amides wherein X=NHR can be produced, for example, by reacting an active ester of a corresponding carboxylic acid with amino-acid amides, or by reacting an active ester of an N-acylamino acid with amines as mentioned in J. Chromatography, vol. 123, p. 149 (1976) or J. Chromatography, vol. 112, p. 121 (1975).

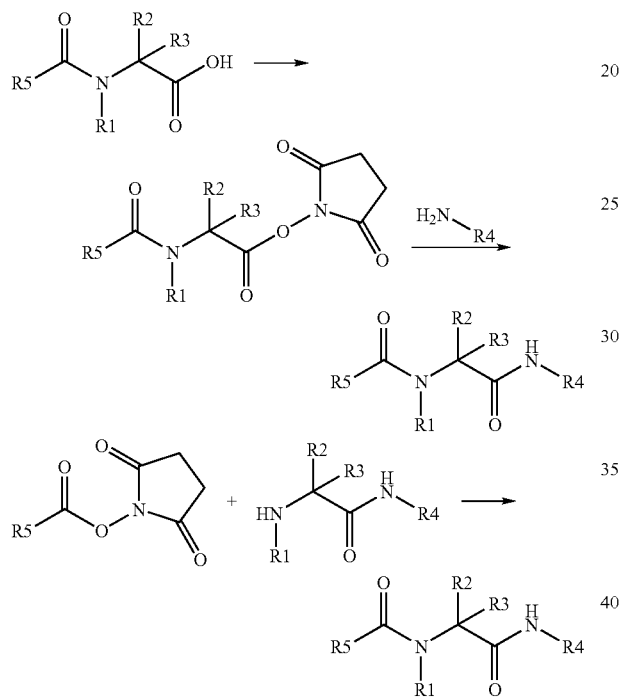

Meanwhile, any methods for producing the compounds of the formula (1) are not limited to the above illustrated production methods.

The present invention provides a PPAR activity regulator, PPAR-α agonist, PPAR-γ agonist or dual agonist of PPAR-α and PPAR-γ, which comprises the above acylamide compound, prodrugs thereof, or pharmaceutically acceptable salts thereof.

In the present invention, preferably about 0.001 to 10000 mg and more preferably about 0.1 to 1000 mg of an acylamide compound can be contained per one preparation. The administered dose differs based on symptoms and age of the administered patient and the administration method, and, in general, 0.1 to 1000 mg/kg/day is preferable.

The administered form of the PPAR activity regulators and activators of the present invention is not particularly limited. The safe and necessary amount thereof can be administered at once or via drip intravenously, intra-arterially, subcutaneously, intramuscularly, or by infusion. Either parenteral or oral administration is possible and the oral administration is preferable from the viewpoint of consideration to patients' pain.

The PPAR activity regulators and activators of the present invention can be formulated into various dosage forms, e.g., in the case of oral agents, dosing preparations such as tablets, capsules, granules, dispersants, trochisci, solutions, subtle granules, injection solvents, cream pharmaceuticals and suppositories. The preparation thereof can be conducted by publicly known methods. Either the active ingredient of the present invention or its preparation may contain pharmaceutically acceptable carriers, diluents, excipients, disintegrating agents, lubricants, flow improvers, or other necessary substances as the preparation. The preparation can be produced by prescribing them, by combination thereof, if necessary. Examples of the preparation carriers include lactose, glucose, D-mannitol, starch, crystalline cellulose, calcium carbonate, kaolin, starch, gelatin, hydroxypropyl cellulose, hydroxypropyl methyl cellulose, polyvinylpyrrolidone, ethanol, carboxy methyl cellulose, carboxy methyl cellulose calcium salts, magnesium stearate, talc, acetyl cellulose, sucrose, titanium oxide, benzoic acid, p-hydroxybenzoate ester, sodium dehydroacetate, gum arabic, tragacanth, methyl cellulose, egg yolk, surfactants, sucrose, simple syrup, citric acid, distilled water, ethanol, glycerin, propylene glycols, macrogol, monobasic sodium phosphate, dibasic sodium phosphate, sodium phosphate, glucose, sodium chloride, phenol, thimerosal, p-hydroxybenzoate ester and acid sodium sulfite. They are used by being mixed with the compounds of the present invention depending on the dosage forms.

The present invention is useful for mammals such as mice, rats, hamsters, rabbits, felines, canines, bovines, sheep, apes and humans as preventive/therapeutic agents of various symptoms derived from hypoadiponectinemia or the decreased expression of adiponectin. Further, the present invention includes commercial packages, including descriptions wherein the acylamide compounds of the present invention should be used.

Next, Examples will further illustrate the present invention. They only explain the present invention and do not particularly limit the invention.

Example 1

Synthetic Example 1

Synthesis of N-lauroyl-L-valine
(Table 1, Compound 20)

294 g (2.51 mol) of L-valine was dissolved into 786 g of ion-exchange water, 358 g (2.42 mol) of an aqueous solution of 27% sodium hydroxide and 363 g of acetone. With stirring the solution, 533 g (2.43 mol) of lauroyl chloride and 358 g (2.47 mol) of an aqueous solution of 27% sodium hydroxide were simultaneously added dropwise thereto so that pH=12±0.2 and the temperature is kept at 19 to 20° C. After completion of the addition, the solution was stirred at 20° C. for 60 minutes. Then, it was heated up to 40° C., and 171 g of 75% sulfuric acid was added thereto in order to adjust pH=1.5. The layers of the oily substance and water phase that separated at 60° C. were split, and 1950 g of warm water of 60° C. was added to the oily substance. After the mixture was cooled down to 20° C., the precipitated solid substance was filtered out and washed with water. Then, the substance was vacuum-dried at 50° C. to obtain 710 g of N-lauroyl-L-valine (2.37 mol, yield 98%).

1H-NMR (CDCl3, 300 MHz) δ (ppm) 0.88 (3H, t, J=6.8 Hz), 0.96 (3H, d, J=6.6 Hz), 0.99 (3H, d, J=6.6 Hz), 1.20-1.40 (16H, br), 1.58-1.74 (2H, br-m), 2.18-2.34 (3H, m), 4.58 (1H, dd, J=4.8 Hz, 8.4 Hz), 6.00 (1H, d, J=8.4 Hz), 7.4-8.6 (1H, br)
ESI-MS [M+H]+ 300

Synthetic Example 2

Synthesis of N-lauroyl-L-valine cyclohexylamide (Table 1, Compound 23)

61 mg (0.20 mmol) of N-lauroyl-L-valine and 39 mg (0.26 mmol) of N-hydroxysuccinimide monohydrate were dissolved into 3.0 mL of dried chloroform. 50 mg (0.26 mmol) of 1-ethyl-3-(3-dimethylpropyl)carbodiimide hydrochloride was added thereto under argon atmosphere and in the ice bath, and stirred at 0° C. for 3 hours. 35 µL of triethylamine and 35 µL of cyclohexylamine were added thereto and stirred at room temperature overnight. Then, 20 mL of ethyl acetate was added thereto and washed with 25 mL of 0.2N hydrochloric acid, 20 mL of water and 20 mL of a saturated aqueous solution of sodium hydrogen carbonate. The mixture was then dried with anhydrous sodium sulfate and condensed under reduced pressure. The residue was purified with a thin-layer chromatography (silica gel, chloroform:methanol=20: 1) to obtain 34 mg of N-lauroyl-L-valine cyclohexylamide (0.089 mmol, yield 44%).

1H-NMR (CDCl3, 300 MHz) δ (ppm) 0.88 (3H, t, J=6.8 Hz), 0.94-0.97 (6H, d*2), 1.08-1.44 (20H, m), 1.55-1.76 (6H, m), 1.80-1.96 (2H, m), 1.96-2.10 (1H, m), 2.21 (2H, t, J=7.8 Hz), 3.65-3.85 (1H, m), 4.15 (1H, dd, J=7.2 Hz, 9.0 Hz), 5.95 (1H, d, J=6.9 Hz), 6.22 (1H, d, J=8.7 Hz)

ESI-MS [M+H]+ 381

Example 1

PPAR-α Agonist Activity

The reporter assay of PPAR (peroxisome proliferator-activated receptor)-α was conducted by using the following plasmids in accordance with the known report (Steven A. Kliwer et al., The Journal of Biological Chemistry Vol. 270, No. 22: 12953-12956, 1995).

As luciferase expressing plasmid, used was the plasmid which introduces the sequence wherein 5 yeast GAL4 binding sequences, UAS (upstream activating sequence), are tandemly connected to the upstream of the thymidine kinase promoter of pTAL-Luc (#6252-1, produced by Clontech) (UAS×5-TK-Luc) (1).

As PPAR-α receptor expressing plasmid, used was the plasmid which introduces the N-terminal domain of human GR (1-76aa), the yeast GAL4 DNA binding domain (1-147aa) and PPAR-α ligand binding domain (167-468aa) to NotI site and SalI site of pExchange-1 core vector (#211176, produced by Stratagene) (hGR-GAL4-hPPAR-α) (2). The plasmid mixed solution used in the reporter assay of PPAR-α contains above (1), (2) and plasmid pcDNA3.1(−) as a carrier in the weight ratio of 4:1:3.

The medium having the following composition was used for seeding cell line CV-1 used in the reporter assay, derived from the kidney of an African green monkey, on the plate; and for diluting the tested compounds. Used was Dulbecco modified Eagle medium (D2902 without phenol red, produced by SIGMA) to which 3.7 g/L of $NaHCO_3$, 3.5 g/L of D-glucose and 10% v/v fetal bovine serum were added.

CV-1 cells were seeded on the 384-well white plate (781080, produced by Greiner) to become $1.5 \times 10^4$ cells/30 µL per one well. Then, gene transfer was conducted in accordance with the manual by using OPTI-MEM I (11058-021, produced by GIBCO), FuGENE6 (1-815-075, produced by Roche) and the above PPAR-α plasmid mixed solution. The incubation was conducted in a carbon-dioxide incubator at 37° C. for 6 to 8 hours. Then, a diluted tested compound was added thereto and incubated in a carbon-dioxide incubator at 37° C. for 16 to 18 hours. Britelite (6016979, produced by PerkinElmer) was further added thereto and stirred, and the luciferase activity was measured with EnVision (produced by PerkinElmer).

Specifying the luciferase activity without addition of a tested compound as 1, the induction ratio of the luciferase activity by each tested compound was calculated. Table 1 shows the induction ratio of each compound in the concentration of 50 µM.

TABLE 1

PPAR-α agonist activity

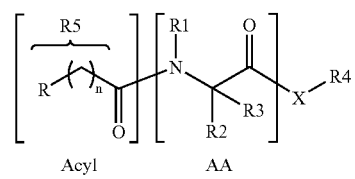

| | Acyl | | AA | | | | | | PPAR-α induction |
| | R5 | | | | | | | | |
| Example | n | R | R1 | D/L | R2 | R3 | X | R4 | ratio |
|---|---|---|---|---|---|---|---|---|---|
| 1 | 6 | CH3 | H | L | Val | | O | H | 1.5 |
| 2 | 7 | CH3 | H | L | Ile | | O | H | 2.1 |
| 3 | 7 | CH3 | H | L | Leu | | O | H | 0.9 |
| 4 | 7 | CH3 | H | L | Val | | O | H | 3.1 |
| 5 | 8 | CH3 | H | L | Ile | | O | H | 3.5 |
| 6 | 8 | CH3 | H | L | Leu | | O | H | 1.3 |
| 7 | 8 | CH2=CH— | H | L | Leu | | O | H | 2.7 |
| 8 | 8 | CH2=CH— | H | L | Phe | | O | H | 1.3 |
| 9 | 8 | CH3 | H | L | Val | | O | H | 19.0 |
| 10 | 8 | CH2=CH— | H | L | Val | | O | H | 23.0 |
| 11 | 9 | CH3 | H | L | Leu | | O | H | 3.0 |
| 12 | 9 | CH3 | H | L | Phe | | O | H | 1.4 |
| 13 | 10 | CH3 | H | DL | Ala | | O | H | 25.0 |

TABLE 1-continued

PPAR-α agonist activity $$\left[\begin{array}{c}R5\\R\left(\right)_n\\O\end{array}\right]\left[\begin{array}{c}R1\ O\\N\\R3\\R2\end{array}\right]X\text{—}R4$$

Acyl      AA

| Example | Acyl R5 | | AA | | | | | | PPAR-α induction ratio |
|---|---|---|---|---|---|---|---|---|---|
| | n | R | R1 | D/L | R2 | R3 | X | R4 | |
| 14 | 10 | CH3 | H | L | Ile | | O | H | 51.0 |
| 15 | 10 | CH3 | H | L | Leu | | O | H | 11.0 |
| 16 | 10 | CH3 | H | DL | Me | Et | O | H | 23.0 |
| 17 | 10 | CH3 | H | — | Me | Me | O | H | 32.0 |
| 18 | 10 | CH3 | H | DL | Me | i-Pro | O | H | 39.0 |
| 19 | 10 | CH3 | H | L | Met | | O | H | 24.0 |
| 20 | 10 | CH3 | H | L | Val | | O | H | 52.0 |
| 21 | 10 | CH3 | H | DL | Val | | NH | H | 45.0 |
| 22 | 10 | CH3 | H | DL | Val | | NH | n-C12H25 | 44.0 |
| 23 | 10 | CH3 | H | DL | Val | | NH | cyclohexyl | 63.0 |
| 24 | 10 | CH3 | C2H5 | L | Val | | O | H | 46.0 |
| 25 | 12 | CH3 | H | L | Ile | | O | H | 50.0 |
| 26 | 12 | CH3 | H | L | Leu | | O | H | 33.0 |
| 27 | 14 | CH3 | H | L | Leu | | O | H | 2.5 |
| 28 | 14 | CH3 | H | L | Val | | O | H | 29.0 |
| 29 | 16 | CH3 | H | L | Leu | | O | H | 1.6 |
| 30 | 16 | CH3 | H | L | Val | | O | H | 15.0 |
| 31 | 20 | CH3 | H | L | Val | | O | H | 1.2 |
| 32 | 8 | CH3 | H | L | t-Bu | H | O | H | 31.5 |
| 33 | 10 | CH3 | H | L | t-Bu | H | O | H | 81.0 |
| 34 | 10 | CH3 | H | DL | —CH(CF3)2 | H | O | H | 2.3 |
| 35 | 10 | CH3 | H | L | allo-Ile | | O | H | 54.7 |
| 36 | 10 | CH3 | H | L | phenyl | H | O | H | 12.5 |
| 37 | 10 | CH3 | H | L | p-methoxyphenylmethyl | H | O | H | 24.5 |
| 38 | 10 | CH3 | H | DL | o-methylphenylmethyl | H | O | H | 2.8 |
| 39 | 10 | CH3 | H | L | cyclohexyl | H | O | H | 2.3 |
| 40 | 10 | CH3 | H | L | diphenylmethyl | H | O | H | 2.0 |
| 41 | 10 | CH3 | H | DL | phenylmethyl | Me | O | H | 7.3 |
| 42 | 10 | CH3 | H | L | p-chlorophenylmethyl | H | O | H | 14.4 |
| 43 | 10 | CH3 | H | L | 3-benzothienylmethyl | H | O | H | 3.0 |
| 44 | 10 | CH3 | H | — | —(CH2)6— | | O | H | 6.2 |

In the table, for example, when R2 and R3 are Val, R2 is a group of —CH(CH$_3$)$_2$ and R3 is a hydrogen atom.

Example 2

PPAR-γ Agonist Activity

The reporter assay of PPAR-γ was conducted by using the following plasmids in accordance with the known report (Steven A. Kliwer et al., The Journal of Biological Chemistry Vol. 270, No. 22: 12953-12956, 1995).

As luciferase expressing plasmid, used was the plasmid which introduces the sequence wherein 5 yeast GAL4 binding sequences, UAS, are tandemly connected to the upstream of the thymidine kinase promoter of pTAL-Luc (#6252-1, produced by Clontech) (UAS×5-TK-Luc) (1).

As PPAR-γ receptor expressing plasmid, used was the plasmid which introduces the N-terminal domain of human GR (1-76aa), the yeast GAL4 DNA binding domain (1-147aa) and PPAR-γ2 ligand binding domain (204-505aa) to NotI site and SalI site of pExchange-1 core vector (#211176, produced by Stratagene) (hGR-GAL4-hPPAR-γ) (2). The plasmid mixed solution used in the reporter assay of PPAR-γ contains above (1), (2) and plasmid pcDNA3.1(–) as a carrier in the weight ratio of 4:1:3.

CV-1 cells were seeded on the 384-well white plate (781080, produced by Greiner) to become 1.5×10$^4$ cells/30 μL per one well. Then, gene transfer was conducted in accordance with the manual by using OPTI-MEM I (11058-021, produced by GIBCO), FuGENE6 (1-815-075, produced by Roche) and the above PPAR-γ plasmid mixed solution. The incubation was conducted in a carbon-dioxide incubator at 37° C. for 6 to 8 hours. Then, a diluted tested compound was added thereto and incubated in a carbon-dioxide incubator at 37° C. for 16 to 18 hours. Britelite (6016979, produced by PerkinElmer) was further added thereto and stirred, and the luciferase activity was measured with EnVision (produced by PerkinElmer).

Specifying the luciferase activity without addition of a tested compound as 1, the induction ratio of the luciferase activity by each tested compound was calculated. Table 2 shows the induction ratio of each compound in the concentration of 25 μM.

TABLE 2

PPAR-γ agonist activity $$\left[R\underset{O}{\overset{R5}{\underbrace{\left(\phantom{x}\right)_n}}}\right]\left[\underset{R2}{\overset{R1\phantom{xx}O}{\underset{|}{\underset{R3}{N}}}}\right]X^{R4}$$

Acyl      AA

| | Acyl | | | | | | | | PPAR-γ |
|---|---|---|---|---|---|---|---|---|---|
| | | R5 | | | AA | | | | induction |
| Example | n | R | R1 | D/L | R2 | R3 | X | R4 | ratio |
| 1 | 6 | CH3 | H | L | Val | | O | H | 11.9 |
| 2 | 7 | CH3 | H | L | Ile | | O | H | 12.5 |
| 3 | 7 | CH3 | H | L | Leu | | O | H | 6.1 |
| 4 | 7 | CH3 | H | L | Val | | O | H | 12.9 |
| 5 | 8 | CH3 | H | L | Ile | | O | H | 15.9 |
| 6 | 8 | CH3 | H | L | Leu | | O | H | 9.5 |
| 7 | 8 | CH2=CH— | H | L | Leu | | O | H | 11.5 |
| 8 | 8 | CH2=CH— | H | L | Phe | | O | H | 4.4 |
| 9 | 8 | CH3 | H | L | Val | | O | H | 25.4 |
| 10 | 8 | CH2=CH— | H | L | Val | | O | H | 15.3 |
| 11 | 9 | CH3 | H | L | Leu | | O | H | 11.6 |
| 12 | 9 | CH3 | H | L | Phe | | O | H | 4.2 |
| 13 | 10 | CH3 | H | DL | Ala | | O | H | 15.4 |
| 14 | 10 | CH3 | H | L | Ile | | O | H | 20.5 |
| 15 | 10 | CH3 | H | L | Leu | | O | H | 9.7 |
| 16 | 10 | CH3 | H | DL | Me | Et | O | H | 18.5 |
| 17 | 10 | CH3 | H | — | Me | Me | O | H | 20.3 |
| 18 | 10 | CH3 | H | DL | Me | i-Pro | O | H | 24.0 |
| 19 | 10 | CH3 | H | L | Met | | O | H | 20.9 |
| 20 | 10 | CH3 | H | L | Val | | O | H | 19.1 |
| 21 | 10 | CH3 | H | DL | Val | | NH | H | 19.2 |
| 22 | 10 | CH3 | H | DL | Val | | NH | n-C12H25 | 16.6 |
| 23 | 10 | CH3 | H | DL | Val | | NH | cyclohexyl | 21.3 |
| 24 | 10 | CH3 | C2H5 | L | Val | | O | H | 16.4 |
| 25 | 12 | CH3 | H | L | Ile | | O | H | 27.4 |
| 26 | 12 | CH3 | H | L | Leu | | O | H | 21.0 |
| 27 | 14 | CH3 | H | L | Leu | | O | H | 11.7 |
| 28 | 14 | CH3 | H | L | Val | | O | H | 17.1 |
| 29 | 16 | CH3 | H | L | Leu | | O | H | 12.3 |
| 30 | 16 | CH3 | H | L | Val | | O | H | 13.7 |
| 31 | 20 | CH3 | H | L | Val | | O | H | 4.4 |
| 32 | 8 | CH3 | H | L | t-Bu | H | O | H | 15.2 |
| 33 | 10 | CH3 | H | L | t-Bu | H | O | H | 30.2 |
| 34 | 10 | CH3 | H | DL | —CH(CF3)2 | H | O | H | 2.7 |
| 35 | 10 | CH3 | H | L | allo-Ile | | O | H | 21.1 |
| 36 | 10 | CH3 | H | L | phenyl | H | O | H | 8.7 |
| 37 | 10 | CH3 | H | L | p-methoxyphenylmethyl | H | O | H | 19.5 |
| 38 | 10 | CH3 | H | DL | o-methylphenylmethyl | H | O | H | 3.2 |
| 39 | 10 | CH3 | H | L | cyclohexyl | H | O | H | 11.2 |
| 40 | 10 | CH3 | H | L | diphenylmethyl | H | O | H | 1.5 |
| 41 | 10 | CH3 | H | DL | phenylmethyl | Me | O | H | 5.1 |
| 42 | 10 | CH3 | H | L | p-chlorophenylmethyl | H | O | H | 6.6 |
| 43 | 10 | CH3 | H | L | 3-benzothienylmethyl | H | O | H | 2.2 |
| 44 | 10 | CH3 | H | — | —(CH2)6— | | O | H | 6.7 |

In the table, for example, when R2 and R3 are Val, R2 is a group of —CH(CH$_3$)$_2$ and R3 is a hydrogen atom.

What is claimed is:

1. A peroxisome proliferator-activated receptor activity regulator, which comprises an acylamide compound of the formula (1), or a pharmaceutically acceptable salt thereof, and at least one pharmaceutically acceptable carrier, diluent, excipient, disintegrating agent, lubricant, and/or flow improver:

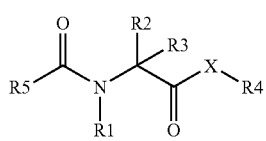

Formula (1)

wherein R1 is a hydrogen atom or an alkyl group having 1 to 6 carbon atoms;

R2 is an alkyl group having 1 to 10 carbon atoms, aryl group having 6 to 10 carbon atoms, arylalkyl group having 7 to 20 carbon atoms, or alkylthioalkyl group having 2 to 6 carbon atoms;

R3 is a hydrogen atom or an alkyl group having 1 to 6 carbon atoms, and R2 and R3 may bond each other to form a ring;

R4 is a hydrogen atom or an alkyl group having 1 to 16 carbon atoms;

R5 is a straight-chain hydrocarbon group having 5 to 21 carbon atoms which may have 1 to 3 double bond(s); and X is NH.

2. A peroxisome proliferator-activated receptor activity regulator according to claim 1, wherein, in the formula (1), R1 is a hydrogen atom or an alkyl group having 1 to 4 carbon atoms; R2 is a straight- or branched-chain alkyl group having 1 to 4 carbon atoms; R3 is a hydrogen atom; R4 is a hydrogen atom, a straight-chain alkyl group having 1 to 16 carbon atoms, a branched-chain alkyl group having 1 to 16 carbon atoms, or a cyclic alkyl group having 3 to 16 carbon atoms; R5 is a straight-chain alkyl group having 5 to 21 carbon atoms which may have one double bond; and X is NH.

3. A method of regulating peroxisome proliferator-activated receptor-α activity, comprising administering an effective amount of a peroxisome proliferator-activated receptor activity regulator according to claim 1 to a subject in need thereof.

4. A method of regulating peroxisome proliferator-activated receptor-γ activity, comprising administering an effective amount of a peroxisome proliferator-activated receptor activity regulator according to claim 1 to a subject in need thereof.

5. A method of regulating peroxisome proliferator-activated receptor-α and -γ activity, comprising administering an effective amount of a peroxisome proliferator-activated receptor activity regulator according to claim 1 to a subject in need thereof.

6. A method of treating a disease selected from the group consisting of diabetes, metabolic syndromes, hyperlipemia, high-blood pressure, vascular disorders, inflammation, hepatitis, fatty liver, liver fibrosis, non-alcoholic steatohepatitis, and obesity, comprising administering an effective amount of a peroxisome proliferator-activated receptor activity regulator according to claim 1 to a subject in need thereof.

7. The method of claim 6, wherein said peroxisome proliferator-activated receptor activity regulator is administered intravenously, intra-arterially, subcutaneously, intramuscularly, or by infusion.

8. The method of claim 6, wherein said peroxisome proliferator-activated receptor activity regulator is administered orally.

9. The method of claim 6, wherein said peroxisome proliferator-activated receptor activity regulator is administered in an amount of 0.1 to 1000 mg per kg by weight of said subject per day.

10. The method of claim 6, wherein said subject is a human.

11. A method of regulating peroxisome proliferator-activated receptor-α activity, comprising administering an effective amount of a peroxisome proliferator-activated receptor activity regulator according to claim 2 to a subject in need thereof.

12. A method of regulating peroxisome proliferator-activated receptor-γ activity, comprising administering an effective amount of a peroxisome proliferator-activated receptor activity regulator according to claim 2 to a subject in need thereof.

13. A method of regulating peroxisome proliferator-activated receptor-α and -γ activity, comprising administering an effective amount of a peroxisome proliferator-activated receptor activity regulator according to claim 2 to a subject in need thereof.

14. A method of treating a disease selected from the group consisting of diabetes, metabolic syndromes, hyperlipemia, high-blood pressure, vascular disorders, inflammation, hepatitis, fatty liver, liver fibrosis, non-alcoholic steatohepatitis, and obesity, comprising administering an effective amount of a peroxisome proliferator-activated receptor activity regulator according to claim 2 to a subject in need thereof.

15. The method of claim 14, wherein said peroxisome proliferator-activated receptor activity regulator is administered intravenously, intra-arterially, subcutaneously, intramuscularly, or by infusion.

16. The method of claim 14, wherein said peroxisome proliferator-activated receptor activity regulator is administered orally.

17. The method of claim 14, wherein said peroxisome proliferator-activated receptor activity regulator is administered in an amount of 0.1 to 1000 mg per kg by weight of said subject per day.

18. The method of claim 14, wherein said subject is a human.

19. The method of claim 3, wherein said peroxisome proliferator-activated receptor activity regulator is administered intravenously, intra-arterially, subcutaneously, intramuscularly, or by infusion.

20. The method of claim 3, wherein said peroxisome proliferator-activated receptor activity regulator is administered orally.

21. The method of claim 3, wherein said peroxisome proliferator-activated receptor activity regulator is administered in an amount of 0.1 to 1000 mg per kg by weight of said subject per day.

22. The method of claim 3, wherein said subject is a human.

23. The method of claim 11, wherein said peroxisome proliferator-activated receptor activity regulator is administered intravenously, intra-arterially, subcutaneously, intramuscularly, or by infusion.

24. The method of claim 11, wherein said peroxisome proliferator-activated receptor activity regulator is administered orally.

25. The method of claim 11, wherein said peroxisome proliferator-activated receptor activity regulator is administered in an amount of 0.1 to 1000 mg per kg by weight of said subject per day.

26. The method of claim 11, wherein said subject is a human.

* * * * *